United States Patent [19]

Ison

[11] Patent Number: Plant 7,294

[45] Date of Patent: Aug. 14, 1990

[54] FARRER

[76] Inventor: William G. Ison, Rte. 1, Box 19, Highway 19, Brooks, Ga. 30205

[21] Appl. No.: 166,249

[22] Filed: Mar. 10, 1988

[51] Int. Cl.[5] ..... A01H 5/00

[52] U.S. Cl. ..... Plt./47

[58] Field of Search ..... Plt. 47

*Primary Examiner*—Robert E. Bagwill

*Attorney, Agent, or Firm*—Eugene T. Holmes

[57] ABSTRACT

A cross between the female variety Farrer and the pollen parent variety Senoia to produce an improved variety of muscadine grape.

1 Drawing Sheet

DESCRIPTION OF THE VARIETY

The new variety is a cross between the female variety Farrer plus pollen parent Senoia.

The primary objective of the breading was to produce an improved variety of muscadine grape; the fruit of which would be large and black. Its characteristics include even ripening, high sugar content, dry scar for longer shelf life, high quality; the plant is productive and vigorous. This new variety is female.

In comparison with the seed parent, the present variety is similar in shape, color and sugar content. The fruit of this new variety contains on the average of from 20.50 to 21.50 soluble solids. The present variety yields approximately 8 to 10 tons of fruit per acre in tests conducted at Ison's Nursery & Vineyards, Brooks, Ga. Outstanding characteristics include excellent flavor. Approximately 15% of fruit is seedless. This variety ripens over a long period of time and is an excellent producer.

Asexual reproduction of the new variety either by soft wood cuttings or by layering as performed at Brooks, Ga. shows that the foregoing characteristics and distinctions come true to form and are established and transmitted through succeeding ropagations.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*
Type: Vine.
Seed parent: Variety Farrer.
Pollen parent: Senoia variety.

Propagation: Holds its characteristics through succeeding propagation by either layering or by soft wood cuttings.
Locality where grown: Brooks, Ga.
Fruit borne: Usually in clusters of 5 to 18 berries.
Fruit size: Large, similar in size to the seed parent, about 1¼" in diameter.
Fruit color: Greyed Purple group, 187A Fan 4 Royal Horticultural Society, London, England.
Sugar content: 20.50 to 21.50 percent soluble solids.
Fruit shape: Oblong.
Seed: Average diameter ⅛ inch, average seed per berry 2.65.
Pulp: Color: Green Group 194B Fan 4 Royal Horticultural Society, London England. Consistency, medium soft; medium juicy as compared to most muscadine varieties.
Reproductive organs: Pistillate-not self pollinating. Note: this is a female variety which can be reproduced from cuttings but when planted will not pollinate other varieties.
Skin: Thin, edible.
Folige: Leaf color, green group 139B Fan 3 Royal Horticultural Society, London, England. Leaf size and shape similar to most muscadine varieties.
Growth habits: Vine requires support; vigorous and productive.
Canes: Small to medium.
Maturity date: Usually ripens about October 3 at Brooks, Ga.
Diseases: Tolerant to Black Rot, Ripe rot and other diseases.

This description was made from a muscadine vine grown at Ison's Nursery & Vineyards, Brooks, Ga.

I claim:

1. The new and distinct variety of grape plant as described and illustrated.

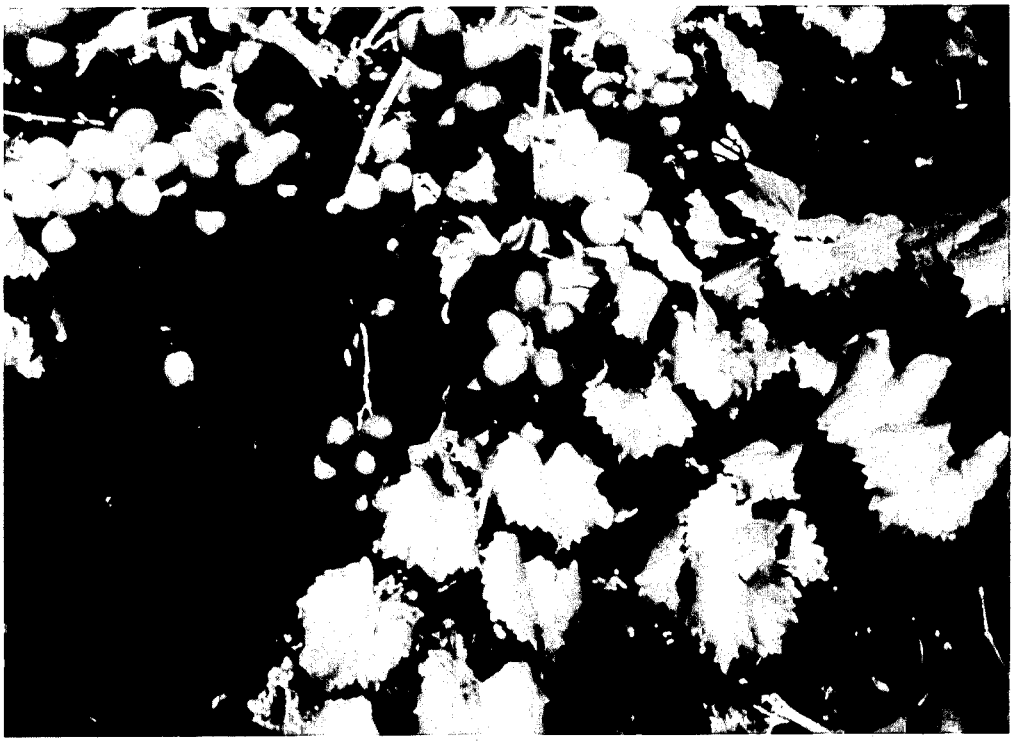

* * * * *